US006447789B1

(12) United States Patent
Banks

(10) Patent No.: US 6,447,789 B1
(45) Date of Patent: Sep. 10, 2002

(54) FACIAL CLEANSER AND METHOD OF TREATING SKIN CONDITIONS

(76) Inventor: Terrie E. Banks, 16609 Halston La., Chesterfield, MO (US) 63005

( * ) Notice: Subject to any disclaimer, the term of this patent is extended or adjusted under 35 U.S.C. 154(b) by 0 days.

(21) Appl. No.: 09/417,378

(22) Filed: Oct. 13, 1999

(51) Int. Cl.$^7$ .................................................. A61K 7/00
(52) U.S. Cl. .......................... 424/401; 424/43; 424/49; 424/70.1; 424/601; 424/722
(58) Field of Search ............................ 424/401, 43, 49, 424/70.1, 601, 722

(56) References Cited

U.S. PATENT DOCUMENTS

| | | | |
|---|---|---|---|
| 4,110,263 A | 8/1978 | Lindemann et al. | 252/545 |
| 4,292,326 A | 9/1981 | Nazzaro-Porro | 424/317 |
| 4,386,104 A | 5/1983 | Nazzaro-Porro | 424/317 |
| 4,885,282 A | 12/1989 | Thornfeldt | 514/53 |
| 4,923,684 A | 5/1990 | Ibrahim et al. | 424/52 |
| 4,963,351 A | 10/1990 | Weston | 424/73 |
| 5,385,943 A | 1/1995 | Nazzaro-Porro | 514/574 |

FOREIGN PATENT DOCUMENTS

WO  WO 94/14406  *  7/1994

OTHER PUBLICATIONS

Lewis, Sr., R.J., Hawley's Condensed Chemical Dictionary, 12$^{th}$ Edition, 1993, 1072 & 1224.*

* cited by examiner

Primary Examiner—Jose' G. Dees
Assistant Examiner—Michael A. Williamson
(74) Attorney, Agent, or Firm—Polster, Lieder, Woodruff & Lucchesi, L.C.

(57) ABSTRACT

A formulation comprising a phosphate salt, particularly sodium tripolyphosphate for cleansing and treating human skin is disclosed. The formulation provides exfoliating properties useful in gently peeling the skin, as well as sequestering properties for removing harmful metals from the skin. The preferred method for the formulations use is also disclosed.

18 Claims, No Drawings

FACIAL CLEANSER AND METHOD OF TREATING SKIN CONDITIONS

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

Several attempts have been made to provide skin treatments that exfoliate and cleanse the skin without abrasives. Recently, the use of alphahydroxy acids (AHA's) such as glycolic, lactic, salicylic or fruit acids have been utilized, with only partial success. The use of AHA's increases skin collagen levels and skin thickness. However, there are side effects common to AHA's. In particular, AHA's may cause stinging, redness, irritation and crusting of the skin. Moreover, reports have emerged connecting AHA's to skin damage including serious skin bums.

Topical formulations comprised of straight, all carbon backbone, dicarboxylic acids have been proposed to replace the fashionable AHA's. Examples of these dicarboxylic acid formulas are found in U.S. Pat. Nos. 4,292,326; 4,386,104, 5,385,943 and 4,885,282.

The problem with use of these dicarboxylic acids is their inherent insolubility in aqueous solutions. Such all carbon backbone, dicarboxylic acids are solids at ambient temperatures, and are extremely difficult to work with, especially with cosmetic or cleanser carriers, the most common of which is water.

There is therefore a need in the art for a class of compounds that can be used as mild, exfoliating actives for topical treatment of skin.

There is also a need in the art for a mild, exfoliating topical composition which contains a water soluble compound that is amenable for manufacturing aesthetically acceptable cosmetic or dermatologic products.

BRIEF SUMMARY OF THE INVENTION

The present invention uses a novel mixture of ingredients to accomplish many of the benefits of AHA's, with fewer side effects, and uses a compound that is readily soluble in water. The present invention uses a phosphate salt, and particularly sodium tripolyphosphate in concentrations of between 0.5 and 40% by weight.

Previously, sodium tripolyphosphate in preferable concentrations of about between 78 to 87% has been added to shaving cream for softening water used in shaving, as described in U.S. Pat. No. 4,963,351 issued to Weston on Oct. 16, 1990. However it has been found that this formulation is inappropriate for cleansing and treatment of skin, because the concentration of sodium tripolyphosphate is too great, and may cause undue irritation of the skin.

Another formulation containing sodium tripolyphosphate is disclosed in U.S. Pat. No. 4,923,684 issued to Ibrahim, et al. on May 8, 1990 for Tripolyphosphate-containing anti-calculus toothpaste, the disclosure of which is incorporated herein by reference. This formulation contains fluoride saccharin and flavor, which are all inappropriate for use on human skin.

Finally, it has long been known that sodium tripolyphosphate is useful for treating meat and poultry, to increase shelf life and aid in retaining color.

DETAILED DESCRIPTION OF INVENTION

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. As various changes could be made in the above constructions without departing from the scope of the invention, it is intended that all matter contained in the above description or shown in the accompanying drawings shall be interpreted as illustrative and not in a limiting sense.

The present invention includes the surprising discovery that the class of compounds tripolyphosphates, and in particular Sodium Tripolyphosphate (STPP) can be used as active principals in topical applications to treat various skin conditions attributed to, accompanied by or exacerbated by abnormal desquamation including dry skin, ichthyosis, lichen simplex chronicus, keratoses, lentigines, melasma, blemished skin, acne, psoriasis, eczema, pruritis, inflammatory dermatoses, striae distensae (i.e. stretch marks), and calluses.

Amounts of the sodium tripolyphosphate may range from 0.5 to 40%, preferably from 1 to 20%, optimally from 1.2 to 5.5% by weight.

As used herein, "topical application" means spreading or laying directly onto the surface of skin; a "topical composition" means a composition intended to be directly layed onto or spread on the surface of skin; an "effective amount" means an amount of a compound or a composition sufficient to induce a positive change (e.g. normalization of desquamation) in the skin condition to be treated such as those attributed to, accompanied or exacerbated by abnormal desquamation; and a "physiologically acceptable vehicle" or a "suitable topical vehicle" mean drugs, cosmetics, medicaments or inert ingredients which the terms describe that are suitable for use in direct contact with human tissues without undue toxicity.

STPP is known to be a-sequestering or chelating agent. The sequestering agent is a chemical composition capable of bonding certain divalent and trivalent metal ions present on the skin. A phosphate chelating agent is capable of tying up iron ($Fe^{2+}$, $Fe^{3+}$), zinc, copper, calcium, magnesium and other typically di- or trivalent metal species.

An exemplary formulation of the present invention involves a known formulation for skin cleansers, such as is disclosed in U.S. Pat. No. 4,110,263 Lindemann, et al. issued Aug. 29, 1978, incorporated by reference herein, with the addition of from about 1–40% by weight sodium tripolyphosphate.

Nutrients may be added to the formulation, including vitamins, such as vitamin B1 (thiamine), vitamin B2 (riboflavin), B6 (pyrodoxine-HCl), vitamin B12 (cyanocobalamin), vitamin D (cholecalcipherol), vitamin E (tocopherol) and mixed tocopherols, nicotinic acid, pantothenic acid and panthenol, folic acid, choline, carnitine as well as cis,cis-linoleic acid, for example.

While theory plays no part in the present invention, it is believed that the triphosphate ligand is capable of penetrating the skin's surface, thereby providing nutrients present in the formula directly to the underlying dermal layer and fortifying the "living" layer of skin, thereby reducing wrinkles and damage, particularly heavy metal poisoning of the cells. It is also hypothesized that the triphosphate component of the present invention may act in DNA repair.

In addition to a phosphate salt, the formulation may also contain emulsifiers that can be cationic, anionic, non-ionic or amphoteric, or a combination thereof. Non-ionic emulsifiers are preferred. Exemplary non-ionic emulsifiers are commercially available sorbitans, alkoxylated fatty alcohols and alkyl polyglycosides. Anionic emulsifiers may include soaps, alkyl sulfates, monoalkyl and dialkyl phosphates, alkyl sulphonates and acyl isethionates.

Examples of thickening agents suitable for use with the present STPP formulas include xanthan gum, xanthan gum brine tolerant, hydroxypropyl cellulose, hydroxyethyl cellulose, cellulose esthers, carrageenans, sodium alginate, carbopol and gum acacia, Sepigel 305 (available from Seppic Co., France), vee-gum or magnesium aluminum silicate. STPP is also compatible with and its utility can be enhanced by humectants, for example urea, glycering, sorbitol, xylitol, PCA, amino acids, certain polyols and other compounds with hygroscopic properties.

STPP can be combined with most conventional emollients such as mineral oil, petrolatum, paraffin, ceresin, ozokerite, microcrystraline wax, perhydrosqualene, dimethyl polysiloxanes, methylphenyl polysiloxanes, silicone-glycol copolymers, triglyceride esters, acetylated monoglycerides, ethoxylated glycerides, alkyl esters of fatty acids, fatty acids and alcohols, lanolin and lanolin derivatives, polyhydric alcohol esters, sterols, beeswax derivatives, polyhydric alcohols and polyethers, and amides of fatty acids.

It is expected that the formula of the present invention may include perfumes or other fragrances. Natural or artificial pigments may be added as well, as coloring agents.

Mild abrasives, such as water-insoluble alkali or alkaline earth metal salts of carbonate, aluminate and silicate may be added to the formulation of the present invention. Especially preferred are silica, and alumina. Amounts of the abrasive will range from 0.5 to 40% by weight.

The use of the formulation of the present invention as a cleanser varies from individual to individual, depending upon factors such as sensitivity, skin type and age. A typical application for use as a cleanser uses an amount of between 1 and 12 grams of cleanser for use on the face. It is to be understood that amounts of slightly under 1 gram and amounts of over 12 grams are contemplated as well, but the above amount of 1 to 12 grams is preferred. The skin is first wetted thoroughly, prior to application of the cleanser. Water is the preferred wetting agent. Next, the cleanser is applied to the skin and rubbed into the skin with the fingertips. An applicator could also be used instead of working the cleanser into the skin with the fingertips. The cleanser is preferably left on the skin for between 1 and 20 minutes, more preferably from between 2 and 10 minutes, most preferably from between 5 and 7 minutes. Finally, the cleanser is removed from the skin, preferably by applying a sufficient amount of water to the skin to dissolve any remaining cleanser and rinse away the remaining cleanser. The removal may be with a washcloth, or with water in the user's cupped hand, or by any other means effective to apply water and rinse the skin.

Treating a skin condition in a human is accomplished in a similar manner to cleansing the skin, with the formulation of the present invention remaining on the skin for a longer period of time. For example, an amount of between 1 and 12 grams of cleanser for use on the face. It is to be understood that amounts of slightly under 1 gram and amounts of over 12 grams are contemplated as well, but the above amount of 1 to 12 grams is preferred. The skin is first wetted thoroughly, prior to application of the formulation. Water is the preferred wetting agent. Next, the formulation is applied to the skin and rubbed into the skin with the fingertips. Again, an applicator could also be used to apply and work the formulation into the skin. The formulation is preferably left on the skin for between 5 to 60 minutes, more preferably from between 7 and 45 minutes, most preferably from between 15 and 20 minutes. Finally, the formulation is removed from the skin, preferably by applying a sufficient amount of water to the skin to dissolve any remaining formulation and rinse away the remaining formulation. The removal may be with a washcloth, or with water in the user's cupped hand, or by any other means effective to apply water and rinse the skin.

Another use for the present invention in as an ingredient in a lotion or ointment. In this embodiment, the formulation for the lotion or ointment contains from between 0.5 to 40% sodium tripolyphosphate, preferably from between 1 to 25% STAT, and most preferably from between 1.2 to 6% STPP. In this embodiment, the user need not wet the skin prior to application of the lotion or ointment. The user will preferably, but not necessarily cleanse the skin prior to application of the lotion or ointment. An effective amount of lotion or ointment is then applied to the affected area, and left on for a period of time, from 1 minute to about 12 hours, preferably from about 15 minutes to 10 hours, most preferably from about 1 to 8 hours. The lotion or ointment is then removed from the skin. The removal may be with a washcloth, or with water in the user's cupped hand, or by any other means effective to apply water and rinse the skin.

Numerous variations will occur to those skilled in the art in light of the above specification. For example, other polyphosphates such as sodium hexametaphosphate, potassium hydrogen phosphate, sodium hydrogen phosphate, disodium pyrophosphate, dipotassium pyrophosphate, tetrasodium pyrophosphate, tetrapotassium pyrophosphate and mixtures of these salts may be used to accomplish the advantageous results obtained with sodium tripolyphosphate. Other appropriate carriers could be used, as well as additional ingredients. These examples are merely illustrative.

In view of the above, it will be seen that the several objects and advantages of the present invention have been achieved and other advantageous results have been obtained.

Having thus described the invention, what is claimed and desired to be secured by Letters Patent is:

1. A topical formulation for use in cleansing the skin of a human having a skin condition involving abnormal desquamation, said topical formulation comprising:
   sodium tripolyphosphate in a desquamation effective amount of between 0.5% and 40% by weight of the formulation;
   a topical vehicle appropriate for application to human skin for carrying said sodium tripolyphosphate; and
   at least one emollient compound.

2. The formulation of claim 1 wherein the concentration of said sodium tripolyphosphate is between 1 and 20% by weight.

3. The formulation of claim 2 wherein the concentration of said sodium tripolyphosphate is between 1 and 5% by weight.

4. The formulation of claim 1 further comprising at least one vitamin compound.

5. The formula of claim 1 further comprising an emulsifier.

6. The formula of claim 5 further comprising a thickening agent.

7. The formulation of claim 6 further comprising a perfume.

8. The formula of claim 7 further comprising a coloring agent.

9. A method of cleansing the skin of a human comprising:
   providing a cleanser containing an emollient compound and a effective amount desquamation of sodium tripolyphosphate;
   applying said cleanser to the skin of a human in an effective amount
   allowing said cleanser to remain on said skin for between 1 and 20 minutes; and
   removing said cleanser from said skin.

10. The method of claim 9 wherein said cleanser is allowed to remain on said skin for between 2 and 5 minutes.

11. A method of treating a human skin condition involving abnormal desquamation in a subject in need of such treatment, said method comprising:
   providing a topical formulation comprising an emollient compound and a desquamation effective amount of between 0.5 and 40% by weight sodium tripolyphosphate for application on human skin;
   applying the formulation to the skin of the subject;
   allowing the formulation to remain on the skin for between about 1 minute and 12 hours;
   removing the formulation from the skin.

12. The method of claim 11 wherein said formulation is allowed to remain on said skin for between about 5 minutes and 10 hours.

13. The method of claim 12 wherein said formulation is allowed to remain on said skin for between about 15 minutes and 8 hours.

14. The method of claim 11 wherein said formulation comprises from between 1 and 25% sodium tripolyphosphate.

15. The method of claim 11 further comprising a step of wetting the skin prior to application of said formulation to said skin.

16. The method of claim 15 wherein said formulation is allowed to remain on said skin from between 7 and 45 minutes.

17. The method of claim 15 wherein said formulation is allowed to remain on said skin from between 15 and 20 minutes.

18. The method of claim 11 wherein the human skin condition comprises a condition selected from the group of dry skin, ichthyosis, lichen simplex chronicus, keratoses, lentigines, melasma, blemished skin, acne, psorisis, eczema, pruritis, inflammatory dematoses, striae distensae and calluses.

* * * * *